United States Patent
Zhao et al.

(10) Patent No.: US 8,129,886 B2
(45) Date of Patent: Mar. 6, 2012

(54) APPARATUS AND METHOD FOR INCREASING SENSITIVITY OF ULTRASOUND TRANSDUCERS

(75) Inventors: Jian Zhong Zhao, Laveen, AZ (US); Alan Chi-Chung Tai, Phoenix, AZ (US); Dwayne Quatier, Chandler, AZ (US); Kevin Mahoney, Phoenix, AZ (US)

(73) Assignee: General Electric Company, Schenectady, NY (US)

( * ) Notice: Subject to any disclaimer, the term of this patent is extended or adjusted under 35 U.S.C. 154(b) by 485 days.

(21) Appl. No.: 12/040,287

(22) Filed: Feb. 29, 2008

(65) Prior Publication Data
US 2009/0219108 A1 Sep. 3, 2009

(51) Int. Cl.
*H01L 41/08* (2006.01)
(52) U.S. Cl. ..................................................... 310/334
(58) Field of Classification Search ............. 310/313 D, 310/313 R, 313 A, 311, 334, 327, 335, 336, 310/337; 324/727; 29/25.35; *H01L 41/08, H01L 41/09*
See application file for complete search history.

(56) References Cited

U.S. PATENT DOCUMENTS

| | | | | |
|---|---|---|---|---|
| 4,771,205 A | * | 9/1988 | Mequio | 310/334 |
| 5,311,095 A | * | 5/1994 | Smith et al. | 310/334 |
| 5,608,692 A | * | 3/1997 | Toda | 310/334 |
| 6,045,506 A | * | 4/2000 | Hossack | 600/443 |
| 6,049,159 A | * | 4/2000 | Barthe et al. | 310/334 |
| 6,685,647 B2 | | 2/2004 | Savord et al. | |
| 7,621,028 B2 | * | 11/2009 | Gelly et al. | 310/334 |

* cited by examiner

*Primary Examiner* — Thomas Dougherty
*Assistant Examiner* — Karen B Addison
(74) *Attorney, Agent, or Firm* — The Small Patent Law Group; Dean D. Small (57) ABSTRACT

An acoustical stack for use within an ultrasound transducer that has a center frequency has a poled piezoelectric material layer and at least one impedance matching layer. The poled piezoelectric material layer has top and bottom sides and is formed of poled piezoelectric material that has a first acoustic impedance. The poled piezoelectric material layer has a first thickness and the acoustical stack has an output electrical impedance based on the first thickness. The impedance matching layers are configured to be attached to the top and bottom sides of the poled piezoelectric material layer and have second or third thicknesses. The impedance matching layers are formed of one or more materials that have an acoustic impedance substantially similar to the first acoustic impedance. The poled piezoelectric layer and impedance matching layers form an acoustic resonance thickness. The center frequency of the transducer is based on the acoustic resonance thickness.

22 Claims, 6 Drawing Sheets

APPARATUS AND METHOD FOR INCREASING SENSITIVITY OF ULTRASOUND TRANSDUCERS

BACKGROUND OF THE INVENTION

This invention relates generally to ultrasound transducers, and more particularly, to acoustical stacks that are within the ultrasound transducers.

Ultrasound transducers (also commonly referred to as probes) typically have many acoustical stacks arranged in one dimension or in two-dimensional (2D) arrays. Each acoustical stack corresponds to an element within the transducer, and a transducer may have many acoustical stacks therein, such as several thousand arranged in the 2D array.

In an array transducer, the electrical impedance of a transducer element is higher than the input electrical impedance of the ultrasonic imaging system. This higher impedance results in low efficiency of electrical energy transfer between the transducer and the system, leading to a lowered sensitivity and degraded transducer performance. The electrical impedance of the transducer element increases as the size of the element decreases, therefore, 2D arrays experience a greater degree of decreased sensitivity as the size of the elements is smaller compared to elements in 1D arrays.

Attempts have been made to better match the impedance of the system, such as by using poled piezoelectric materials having a high dielectric constant. Additionally, a multi-poled piezoelectric material layer with a complex electrode design and D-matching layers structure has been used. However, complex electrical connections are needed, increasing the overall complexity, especially for 2D arrays.

Therefore, a need exists for reducing the electrical impedance associated with transducer elements within an ultrasound transducer to improve the sensitivity of the ultrasound system.

BRIEF DESCRIPTION OF THE INVENTION

In one embodiment, an acoustical stack for use within an ultrasound transducer that has a center frequency comprises a poled piezoelectric material layer and a first impedance matching layer. The poled piezoelectric material layer has top and bottom sides and is formed of poled piezoelectric material that has a first acoustic impedance. The poled piezoelectric material layer has a first thickness and the acoustical stack has an output electrical impedance based on the first thickness. The first impedance matching layer is configured to be attached to one of the top and bottom sides of the poled piezoelectric material layer and has a second thickness. The first impedance matching layer is formed of a material that has an acoustic impedance substantially similar to the first acoustic impedance. The poled piezoelectric material layer and the first impedance matching layer form an acoustic resonance thickness. The center frequency of the transducer is based on the acoustic resonance thickness.

In another embodiment, an acoustical stack for use within an ultrasound transducer that has a center frequency comprises a poled piezoelectric material layer and first and second impedance matching layers. The poled piezoelectric material layer has top and bottom sides and has a first acoustic impedance. The poled piezoelectric material layer has a first thickness and the acoustical stack has an output electrical impedance based on the first thickness. The first impedance matching layer has top and bottom sides and a second thickness. The bottom side is configured to be attached to the top side of the poled piezoelectric material layer. The second impedance matching layer has top and bottom sides and has a third thickness. The top side of the second impedance layer is configured to be attached to the bottom side of the poled piezoelectric material layer. The first and second impedance matching layers are formed of first ad second materials that have the first acoustic impedance. The poled piezoelectric material layer and the first and second impedance matching layers form an acoustic resonance thickness upon which the center frequency of the transducer is based.

In yet another embodiment, a method for decreasing output electrical impedance associated with a transducer element comprises defining at least one of a center frequency and a range of operating frequencies associated with an ultrasound transducer. An acoustic resonance thickness based on at least one of a center frequency and range of operating frequencies is identified. A poled piezoelectric material layer having a top and a bottom is formed of a poled piezoelectric material having a first acoustic impedance and a first thickness. At least one impedance matching layer is formed along one of the top and bottom of the poled piezoelectric material layer. The at least one impedance matching layer is formed of a material having substantially the first acoustic impedance. At least one impedance matching layer has a second thickness and the first and second thicknesses are combined to form the acoustic resonance thickness.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 1:
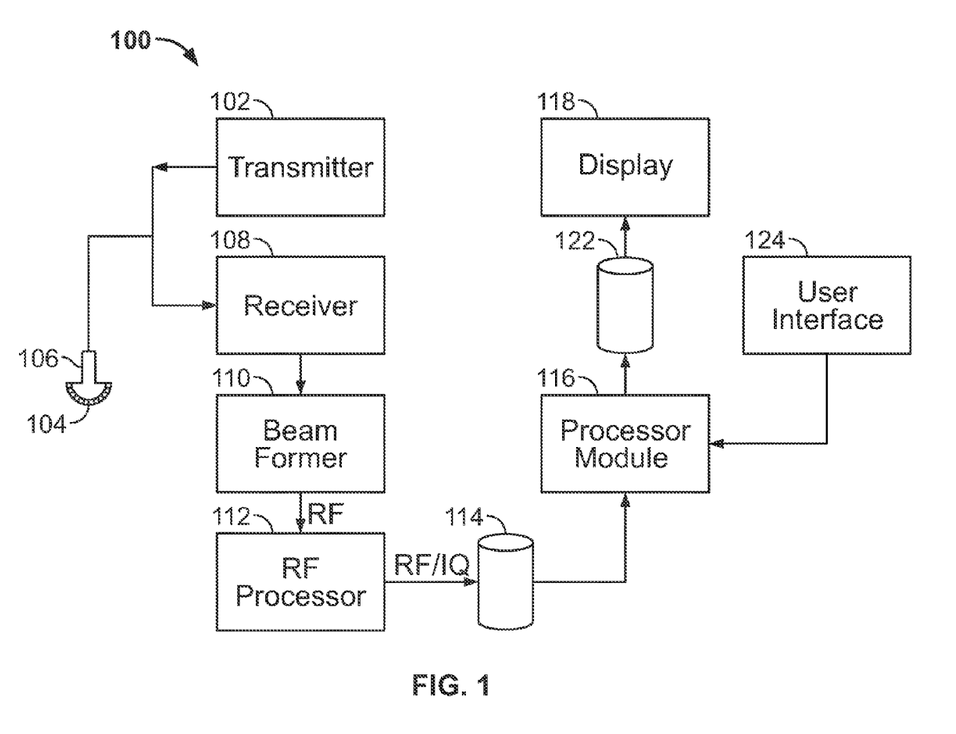
FIG. 1 is a block diagram of an ultrasound system formed in accordance with various embodiments of the present invention.
Figure 3:
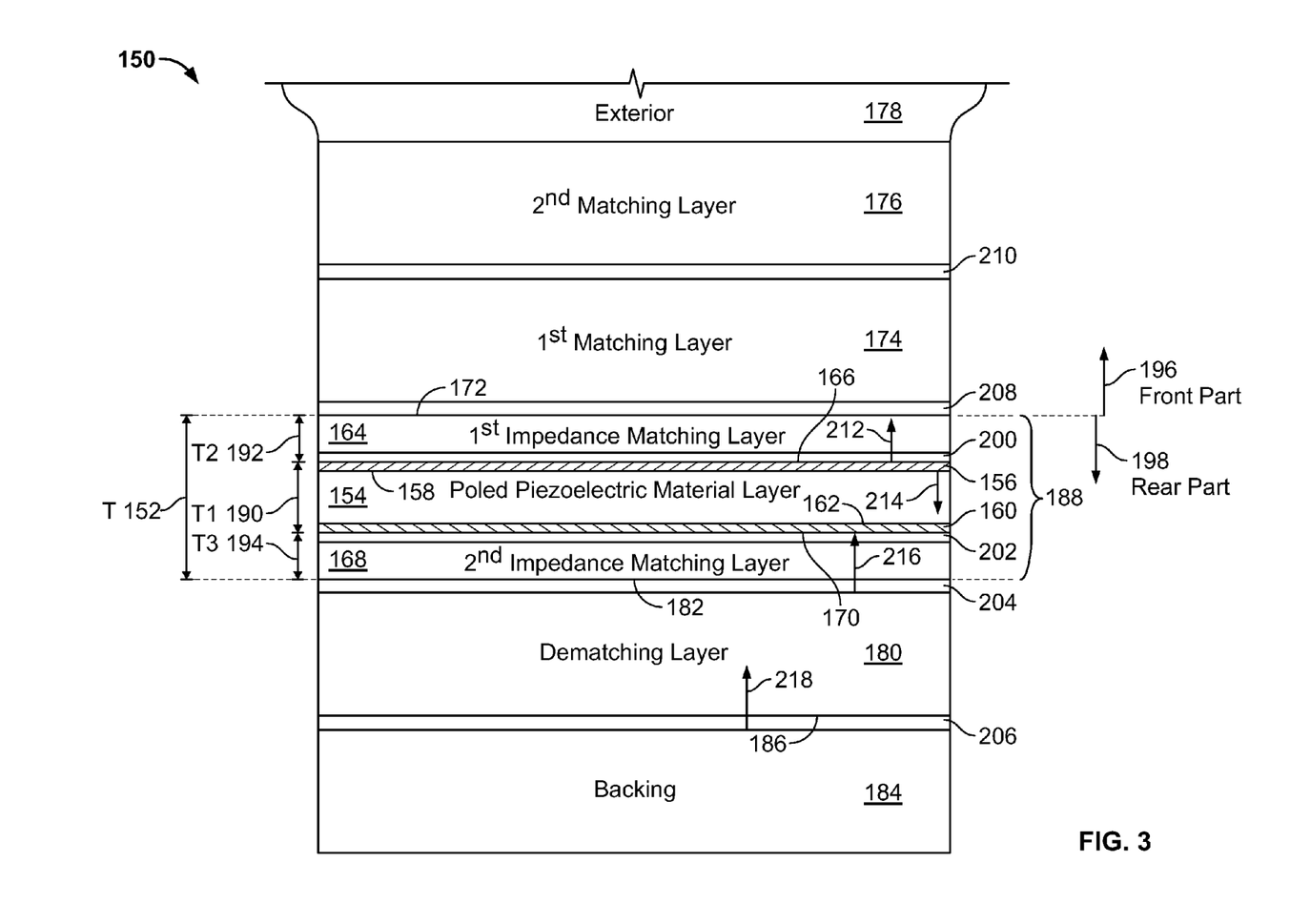
FIG. 3 illustrates an acoustical stack formed in accordance with an embodiment of the present invention that is used within a transducer as shown in FIGS. 1 and 2.

FIG. 1 illustrates an ultrasound system 100 including a transmitter 102 that drives an array of elements 104 within a transducer 106 to emit pulsed ultrasonic signals into a body. Each of the elements 104 corresponds to an acoustical stack (as shown in FIG. 3). The elements 104 may be arranged, for example, in one or two dimensions. A variety of geometries may be used. Each transducer 106 has a defined center operating frequency and/or range of operating frequencies. The ultrasonic signals are back-scattered from structures in the body, like fatty tissue or muscular tissue, to produce echoes that return to the elements 104. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to a memory 114 for storage.

The ultrasound system 100 also includes a processor module 116 to process the acquired ultrasound information (e.g., RF signal data or IQ data pairs) and prepare frames of ultrasound information for display on display 118. The processor module 116 is adapted to perform one or more processing operations according to a plurality of selectable ultrasound modalities on the acquired ultrasound information. Acquired ultrasound information may be processed and displayed in real-time during a scanning session as the echo signals are received. Additionally or alternatively, the ultrasound information may be stored temporarily in memory 114 during a scanning session and then processed and displayed in an off-line operation.

The processor module 116 is connected to a user interface 124 that may control operation of the processor module 116. The display 118 includes one or more monitors that present patient information, including diagnostic ultrasound images to the user for diagnosis and analysis. One or both of memory 114 and memory 122 may store three-dimensional (3D) data sets of the ultrasound data, where such 3D datasets are accessed to present 2D and 3D images. Multiple consecutive 3D datasets may also be acquired and stored over time, such as to provide real-time 3D or 4D display. The images may be modified and the display settings of the display 118 also manually adjusted using the user interface 124.

Figure 2:
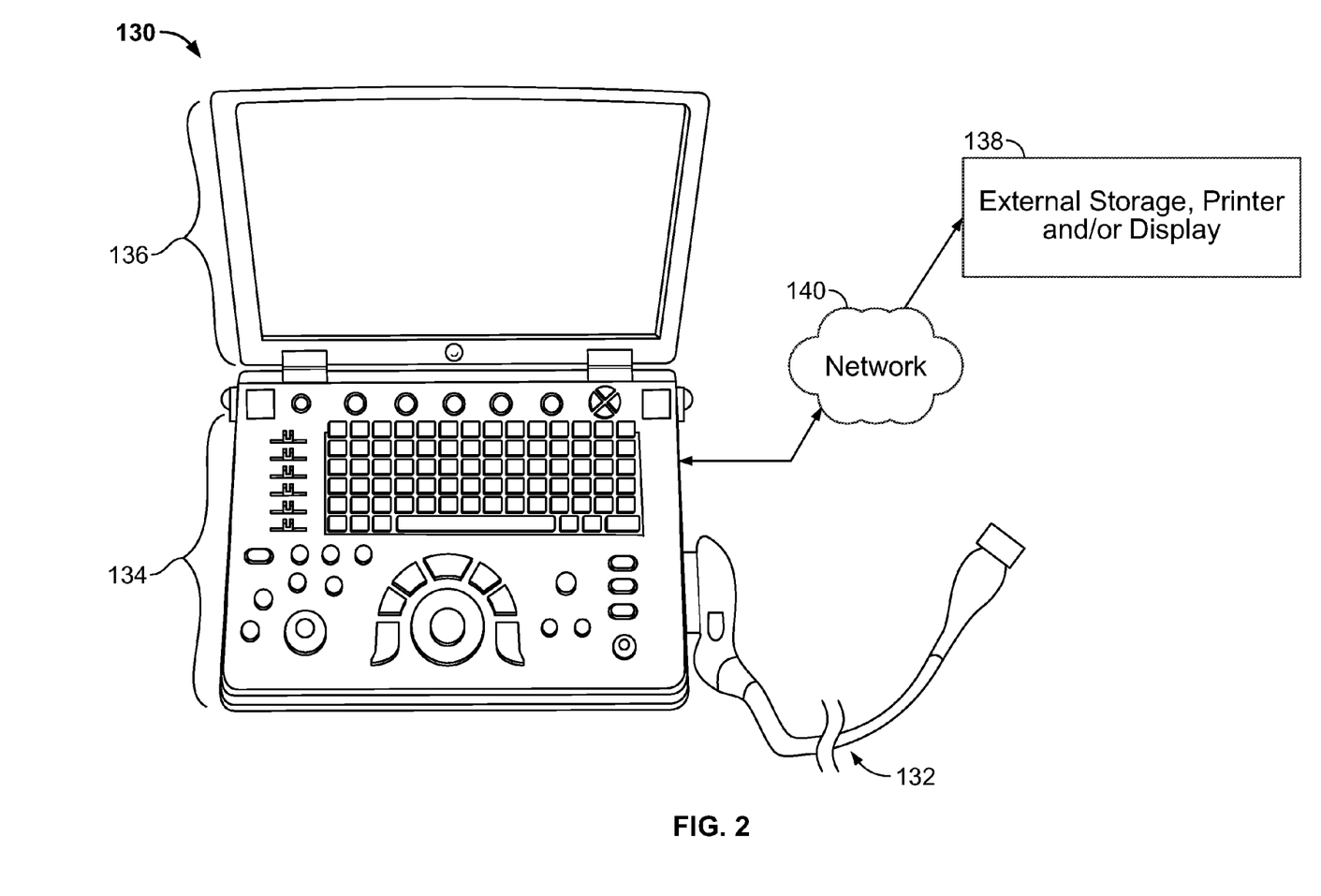
FIG. 2 is a miniaturized ultrasound system formed in accordance with various embodiments of the present invention.

FIG. 2 illustrates a 3D-capable miniaturized ultrasound system 130 having a transducer 132 that may be configured to acquire 3D ultrasonic data. For example, the transducer 132 may have a 2D array of transducer elements 104 as discussed previously with respect to the transducer 106 of FIG. 1. A user interface 134 (that may also include an integrated display 136) is provided to receive commands from an operator. As used herein, "miniaturized" means that the ultrasound system 130 is a handheld or hand-carried device or is configured to be carried in a person's hand, pocket, briefcase-sized case, or backpack. For example, the ultrasound system 130 may be a hand-carried device having a size of a typical laptop computer, for instance, having dimensions of approximately 2.5 inches in depth, approximately 14 inches in width, and approximately 12 inches in height. The ultrasound system 130 may weigh about ten pounds, and thus is easily portable by the operator. The integrated display 136 (e.g., an internal display) is also provided and is configured to display a medical image.

The ultrasonic data may be sent to an external device 138 via a wired or wireless network 140 (or direct connection, for example, via a serial or parallel cable or USB port). In some embodiments, external device 138 may be a computer or a workstation having a display. Alternatively, external device 138 may be a separate external display or a printer capable of receiving image data from the hand carried ultrasound system 130 and of displaying or printing images that may have greater resolution than the integrated display 136.

As another example, the ultrasound system 130 may be a 3D capable pocket-sized ultrasound system. By way of example, the pocket-sized ultrasound system may be approximately 2 inches wide, approximately 4 inches in length, and approximately 0.5 inches in depth and weigh less than 3 ounces. The pocket-sized ultrasound system may include a display, a user interface (i.e., keyboard) and an input/output (I/O) port for connection to the transducer (all not shown). It should be noted that the various embodiments may be implemented in connection with a miniaturized ultrasound system having different dimensions, weights, and power consumption.

FIG. 3 illustrates an acoustical stack 150 that is used within a transducer 106 as shown in FIG. 1. The acoustical stack 150 has several layers attached together in a stacked configuration. As discussed previously, each transducer 106 may have many acoustical stacks 150 and each of the elements 104 within the transducer 106 corresponds to an acoustical stack 150.

An acoustic resonance thickness T 152 may be defined based on a desired center frequency or desired range of operating frequencies. Previously, the thickness of the poled piezoelectric layer used within an acoustical stack of a transducer was the same as the acoustic resonance thickness T 152, and thus the output electrical impedance of the element 104 was also based on the acoustic resonance thickness T 152.

In FIG. 3, however, the acoustic resonance thickness T 152 corresponds to a thickness of an S-matching layer 188 within the acoustical stack 150. A poled piezoelectric material layer 154 and first and second impedance matching layers 164 and 168 together form the S-matching layer 188, wherein the poled piezoelectric material layer 154 is sandwiched between two layers of unpoled material. The poled piezoelectric material layer 154 has a thickness T1 190, the first impedance matching layer 164 has a thickness T2 192, and the second impedance matching layer 168 has a thickness T3 194.

The poled piezoelectric material layer 154 and the first and second impedance matching layers 164 and 168 have the same or substantially similar acoustic impedance with respect to each other. Therefore, the S-matching layer 188 will acoustically resonate at the acoustic resonance thickness T 152, which is a sum of all of the thicknesses of the layers within the S-matching layer 188. However, as the thickness T1 190 of the poled piezoelectric material layer 154 is thinner than the acoustic resonance thickness T 152, the output electrical impedance of the element 104 is reduced at the same center frequency. Also, as the acoustic resonance thickness T 152 may correspond to the thickness of a previously used single layer of poled piezoelectric material, the S-matching layer 188 may easily replace the previously used single layer of poled material during manufacturing.

The poled piezoelectric material layer 154 may be formed of a piezoelectric material such as lead zirconate titanate piezoelectric ceramic material. Other piezoelectrical material or piezocomposite material may be used, such as single crystal (e.g. PMN-PT, PZN-PT), PZT composite, piezoelectric polymer, ceramic composites, single crystal composites, monolithic or multi-layer structure, and the like) may be used. A first electrode 156 may be formed with a thin metallic layer and is deposited on front face 158 of the poled piezoelectric material layer 154. A second electrode 160 is deposited on rear face 162 of the poled piezoelectric material layer 154.

The first impedance matching layer 164 is attached to top side 166 of the poled piezoelectric material layer 154. The second impedance matching layer 168 is attached to bottom side 170 of the poled piezoelectric material layer 154. The first and second impedance matching layers 164 and 168 may also be referred to as end caps. The first and second impedance matching layers 164 and 168 are formed of one or more materials that have the same or substantially the same acoustic impedance of the material forming the poled piezoelectric material layer 154. By having the same, substantially the same, or substantially similar acoustic impedances, waves generated within the acoustical stack 150 by energizing the first and second electrodes 156 and 160 will not be reflected, or will experience a very low amount of reflection, at the boundaries between the layers.

In one embodiment, the first and second impedance matching layers 164 and 168 are formed of unpoled piezoelectric material wherein the unpoled piezoelectric material is the same piezoelectric material forming the poled piezoelectric material layer 154. In another embodiment, the first and second impedance matching layers 164 and 168 may be formed of different material(s) than the poled piezoelectric material layer 154. The layers 164 and 168 may be formed of a single material or a composite or alloy of more than one material, such as having one or more of ceramic and/or metallic materials. In yet another embodiment, one or both of the first and second impedance matching layers 164 and 168 may be formed of more than one layer of material.

At least one matching layer is attached to top side 172 of the first impedance matching layer 164. In the example of FIG. 3, first and second matching layers 174 and 176 are attached to the top side 172 of the first impedance matching layer 164 to match the acoustic impedances between the stack 150 and an exterior 178, which may be based on the acoustic impedance of a human or other subject to be scanned. In other embodiments, there may be one matching layer or more than two matching layers. In some embodiments, a dematching layer 180 is interconnected at a bottom side 182 of the second impedance matching layer 168 and a backing 184 is attached at a bottom side 186 of the dematching layer 180. The dematching layer 180 has high acoustic impedance (e.g. approximately 100 Mray) and may be formed of a material such as Tungsten Carbide.

The stack 150 may be divided into front and rear parts 196 and 198 with respect to the top side 172 of the first impedance matching layer 164. The layers of the stack 150 are acoustically joined together with one or more materials such as glue, adhesive, solder or other assembly layer material. The assembly layer material is shown as assembly layers 200-210. Within the S-matching layer 188, the assembly layer 200 joins the first impedance matching layer 164 and the poled piezoelectric material layer 154, and the assembly layer 202 joins the poled piezoelectric material layer 154 and the second impedance matching layer 168. Further in the rear part 198, the assembly layer 204 joins the second impedance matching layer 168 and the dematching layer 180, and the assembly layer 206 joins the dematching layer 180 and the backing 184. In the front part 196, the assembly layer 208 joins the first impedance matching layer 164 and the first matching layer 174, and the assembly layer 210 joins the first and second matching layers 174 and 176.

When the first and second electrodes 156 and 160 are polarized, the poled piezoelectric material of the poled piezoelectric material layer 154 is electrically excited, generating first and second mechanical waves 212 and 214 that start from the top side 166 of the poled piezoelectric material layer 154. The first mechanical wave 212, which may also be called an initial front wave, is directed toward the front part 196 of the stack 150 and the second mechanical wave 214 is directed toward the rear part 198 of the stack 150. The first mechanical wave 212 will not be reflected at the boundary between the poled piezoelectric material layer 154 and the first impedance matching layer 164 as the acoustic impedances of the layers are the same or substantially similar. Similarly, the second mechanical wave 214 will not be reflected at the boundary between the poled piezoelectric material layer 154 and the second impedance matching layer 168.

The acoustic impedance of the dematching layer 180 and/or backing 184 may be much larger than the acoustic impedance of the S-matching layer 188. When the second mechanical wave 214 reaches the dematching layer 180, the strong mismatch in impedance between the second impedance matching layer 168 and the dematching layer 180 generates a first reflected wave 216, resulting in only a minor quantity of energy leak inside the backing 184. In one embodiment, the thickness of one or more of the stack layers may be chosen to allow constructive phase matching between the first mechanical wave 212 and the first reflected wave 216. As discussed previously, the stack 150 may be constructed without the dematching layer 180. In this configuration, the second mechanical wave 214 would generate reflected wave 218. Although not shown, other, much smaller reflected waves may occur at the interfaces between the layers of the stack 150 and the assembly layers 200-210.

Figure 4:
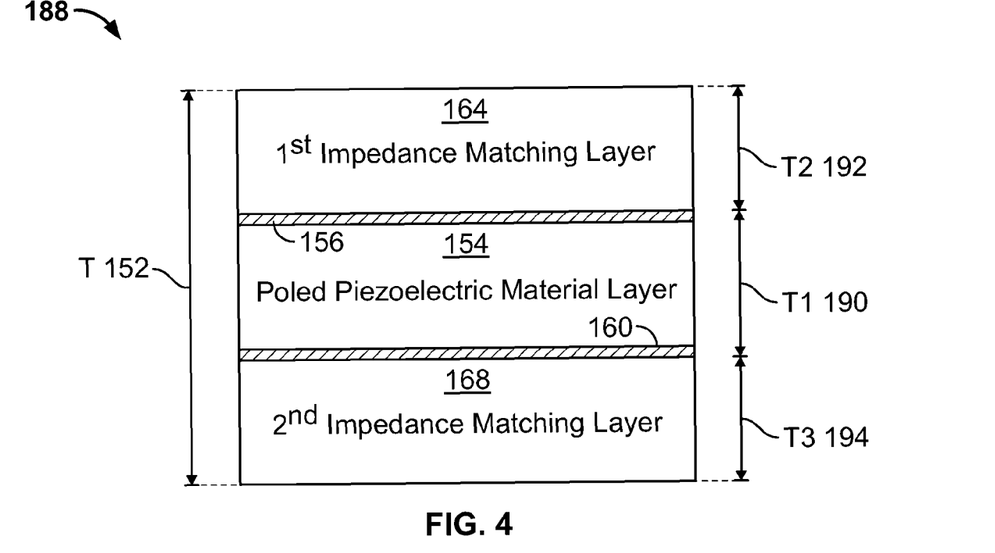
FIG. 4 illustrates exemplary thicknesses of layers within the S-matching layer of the acoustical stack formed in accordance with an embodiment of the present invention.

FIG. 4 illustrates exemplary thicknesses of layers within the S-matching layer 188 of FIG. 3. In this example, the assembly layers 200 and 202 are not shown. The S-matching layer 188 again has the acoustic resonance thickness T 152, which determines the acoustic frequency of the transducer 106. The thickness T1 190 of the poled piezoelectric material layer 154 may be approximately one-half of the acoustic resonance thickness T 152, and the thickness T2 192 and thickness T3 194 may each be approximately one-quarter of the acoustic resonance thickness T 152.

Figure 5:
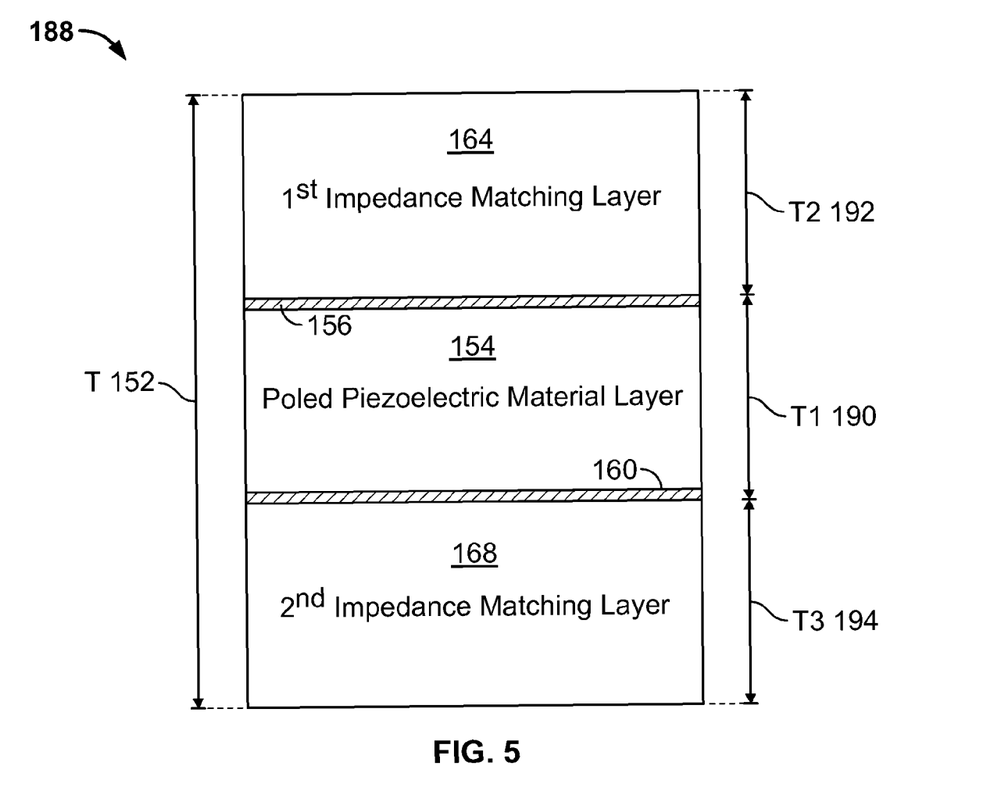
FIG. 5 illustrates different exemplary thicknesses of the layers within the S-matching layer in accordance with another embodiment of the present invention.

FIG. 5 illustrates different exemplary thicknesses of the layers within the S-matching layer 188. In this example, the thickness T1 190, the thickness T2 192 and the thickness T3 194 may all be approximately the same such as one-third of the acoustic resonance thickness T 152. Therefore, it should be understood that the thicknesses T1, T2 and T3 may be varied with respect to each other. However, the sum of the thicknesses T1, T2 and T3 will be equal to or approximately equal to the acoustic resonance thickness T 152. Also, thickness T1 190 may be less than one-third or less than one-quarter of the total acoustic resonance thickness T 152, and may be selected based on desired output electrical impedance.

Figure 6:
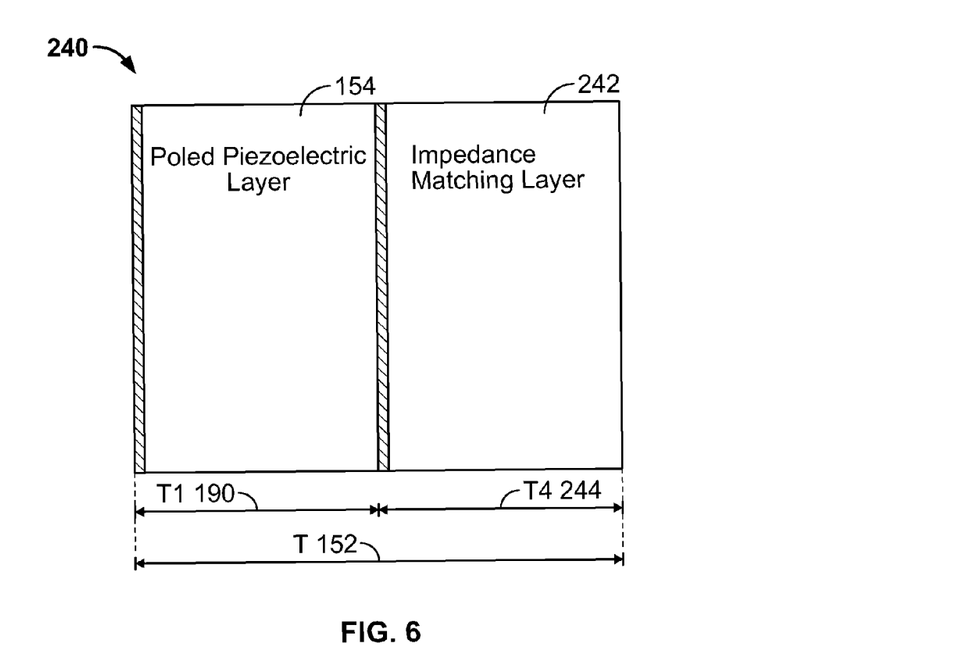
FIG. 6 illustrates an alternative configuration of layers that may form the S-matching layer in accordance with an embodiment of the present invention.

FIG. 6 illustrates an alternative configuration of layers that may form an S-matching layer 240. The S-matching layer 240 may be used within the stack 150 of FIG. 1 instead of the S-matching layer 188. The S-matching layer 240 has the poled piezoelectric material layer 154 and a single impedance matching layer 242. Again, the thickness TI 190 and thickness T4 244 together equal the acoustic resonance thickness T 152. The thickness T1 190 and thickness T4 244 may be varied to achieve a desired output electrical impedance. Also, the poled piezoelectric material layer 154 may be positioned to interface with either the first matching layer 174 or the dematching layer 180 of FIG. 1, positioning the poled piezoelectric material layer 154 within the S-matching layer 240 closer to the front or rear part 196 and 198, respectively, of the stack 150.

By way of example only, when designing a transducer 106 the desired operating or center frequency or range of operating frequencies may first be defined. An acoustic resonance thickness T 152 may be determined for the desired transducer stack structure for the particular operating frequency or range of operating frequencies. The number of layers within the S-matching layer 188 may be selected, such as the poled piezoelectric material layer 154 and the first and second impedance matching layers 164 and 168. The thickness T1 of the poled piezoelectric material layer 154 may be determined, such as based on the desired output electrical impedance and optionally other operating parameters.

In one embodiment, the position of the poled piezoelectric material layer 154 within the S-matching layer 188 may be adjusted by increasing and decreasing the thicknesses of each of the first and second impedance matching layers 164 and 168. This may be done, for example, to accomplish minor phase matching adjustments between the mechanical waves and reflected waves.

Figure 7:
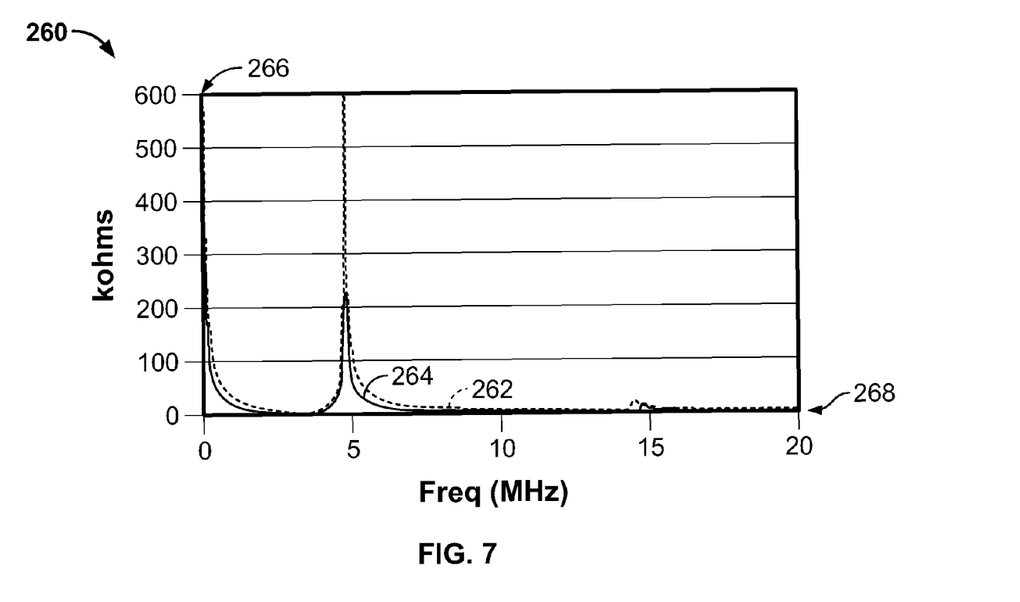
FIG. 7 illustrates frequency responses of different stack configurations in accordance with an embodiment of the present invention.

In FIG. 7, a comparative simulation 260 illustrates frequency responses of different stack configurations. Output electrical impedance is shown along vertical axis 266 and resonance frequency (center frequency) is shown along horizontal axis 268. Line 262 indicates modeled transducer performance using a standard poled piezoelectric thickness of 400 microns. Therefore, line 262 is not associated with the acoustic stack 150 that has the S-matching layer 188, but rather an acoustical stack that uses a single layer of poled piezoelectric material (not shown). Line 264 indicates transducer performance using the S-matching layer 188 wherein the thickness of the poled piezoelectric material layer 154 is 200 microns and the thickness of each of the unpoled piezoelectric material layers, the first and second impedance matching layers 164 and 168, is 100 microns. The lines 262 and 264 indicate similar resonance or center frequency of 5 MHz for each configuration, while indicating that the S-matching layer 188 (line 264) has a lower electrical impedance.

Figure 8:
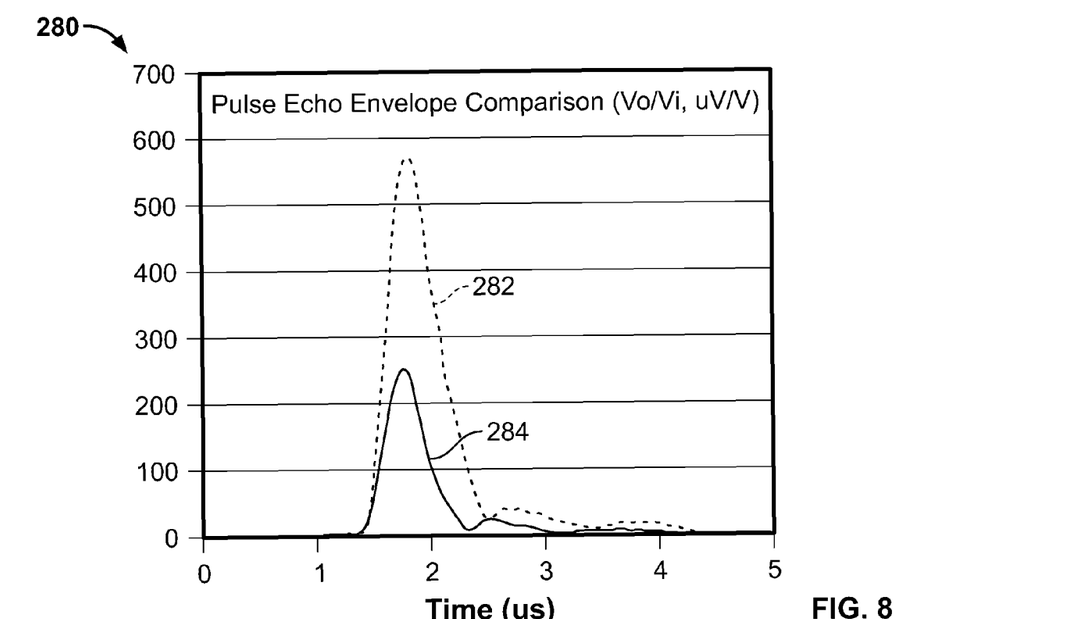
FIGS. 8 and 9 illustrate that the S-matching layer formed in accordance with an embodiment of the present invention improves sensitivity compared to a stack configuration having a single layer of poled piezoelectric material.
Figure 9:
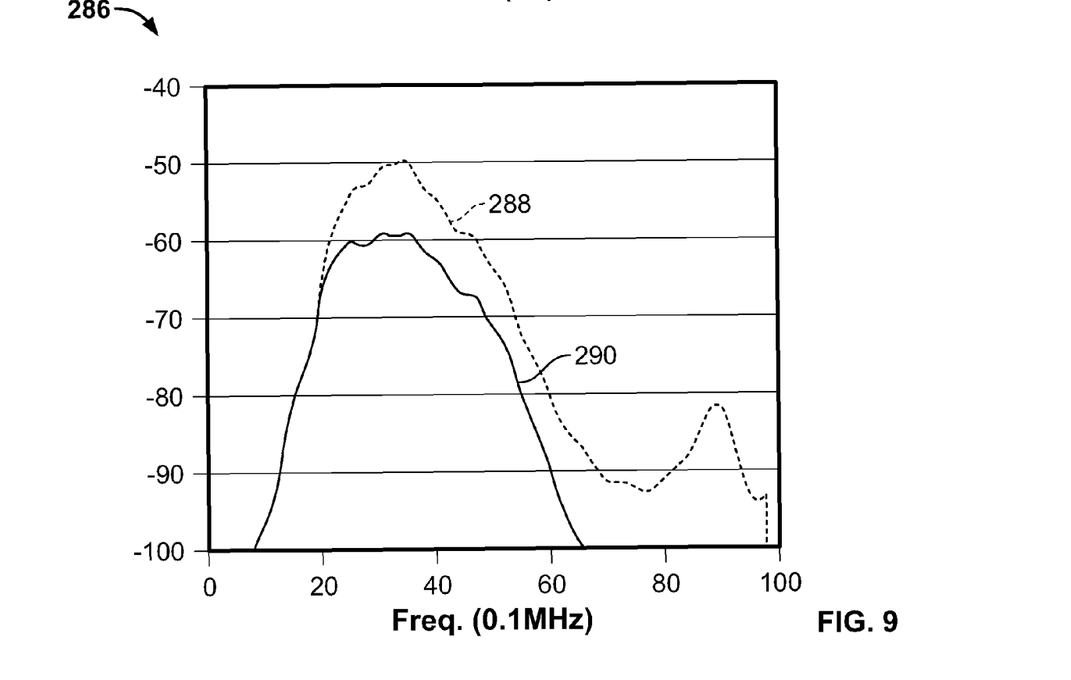

FIGS. 8 and 9 illustrate that the acoustical stack using the S-matching layer 188 has improved sensitivity compared to a stack configuration using the single layer of poled piezoelectric material. In this example, the same layer thicknesses were used as in FIG. 7. Graph 280 illustrates a pulse echo envelope comparison wherein line 282, corresponding to the S-matching layer 188 configuration, has improved sensitivity and a similar pulse length when compared to line 284. Line 284 corresponds to the single layer of poled piezoelectric material whose thickness determines both the acoustic resonance frequency and the output electrical impedance. Graph 286 illustrates that the S-matching layer 188, represented by line 288, has approximately 7 dB higher sensitivity than the single poled piezoelectric material layer, represented by line 290, while having approximately the same center frequency.

A technical effect of at least one embodiment is the improvement of the sensitivity of an ultrasound transducer. The output electrical impedance of a transducer element is related to the thickness of the poled piezoelectric material layer within the acoustical stack and is typically much higher than the electrical impedance of the ultrasound system. By reducing the thickness of the poled piezoelectric material layer, the electrical impedance of the element is reduced. One or more layers of material having substantially the same acoustic impedance as the poled piezoelectric material layer are sandwiched with the poled piezoelectric material layer to form a layer that has a thickness corresponding to the desired operating frequency. Therefore, the thinner poled piezoelectric material layer has reduced output electrical impedance that is closer to that of the ultrasound system, improving sensitivity and performance at a desired operating frequency or range of frequencies.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An acoustical stack for use within an ultrasound transducer that has a center frequency, comprising:
   a poled piezoelectric material layer comprising poled piezoelectric material having a first acoustic impedance, the poled piezoelectric material layer having top and bottom sides and a first thickness, the acoustical stack having an output electrical impedance based on the first thickness; and
   a first impedance matching layer configured to be attached to one of the top and bottom sides of the poled piezoelectric material layer, the first impedance matching layer having a second thickness, the first impedance matching layer formed of a material having an acoustic impedance that is substantially similar to the first acoustic impedance, the poled piezoelectric material layer and the first impedance matching layer forming an acoustic resonance thickness, the center frequency of the transducer based on the acoustic resonance thickness;
   a second impedance matching layer configured to be attached to an opposite side of the poled piezoelectric material layer than the first impedance matching layer, wherein the poled piezoelectric material layer and the first and second impedance matching layers having a non-descending acoustic impedance.

2. The acoustical stack of claim 1, wherein the second impedance matching layer having a third thickness, the second impedance matching layer formed of a material having an acoustic impedance that is substantially similar to the first acoustic impedance, wherein the acoustic resonance thickness is based on the first, second and third thicknesses.

3. The acoustical stack of claim 1, wherein the material forming the first impedance matching layer comprises an unpoled piezoelectric material.

4. The acoustical stack of claim 1, further comprising first and second electrodes configured to interface with the top and bottom sides of the poled piezoelectric material layer, wherein one of the first and second electrodes is between the poled piezoelectric material layer and the first impedance matching layer.

5. The acoustical stack of claim 1, further comprising:
   at least a first matching layer configured to be attached to one of the poled piezoelectric material layer and the first impedance matching layer; and
   at least a backing layer configured to be attached to the other of the poled piezoelectric material layer and the first impedance matching layer.

6. An acoustical stack for use within an ultrasound transducer that has a center frequency, comprising:
   a poled piezoelectric material layer having top and bottom sides, the poled piezoelectric material layer having a first acoustic impedance and a first thickness, the acoustical stack having an output electrical impedance based on the first thickness;
   a first impedance matching layer having top and bottom sides, the bottom side of the first impedance matching layer configured to be attached to the top side of the poled piezoelectric material layer, the first impedance matching layer having a second thickness; and
   a second impedance matching layer having top and bottom sides, the top side of the second impedance layer configured to be attached to the bottom side of the poled piezoelectric material layer, the second impedance matching layer having a third thickness, the first and second impedance matching layers formed of first and second materials that have the first acoustic impedance, the poled piezoelectric material layer and the first and second impedance matching layers forming an acoustic resonance thickness, the center frequency being based on the acoustic resonance thickness, wherein the poled piezoelectric material layer and the first and second impedance matching layers having a non-descending acoustic impedance.

7. The acoustical stack of claim 6, wherein the poled piezoelectric material layer and the first and second impedance matching layers comprise a piezoelectric material, the piezoelectric material being poled in the poled piezoelectric material layer and unpoled in the first and second impedance matching layers.

8. The acoustical stack of claim 6, wherein the first thickness is one-half of the acoustic resonance thickness and the second and third thicknesses are each approximately one-quarter of the acoustic resonance thickness.

9. The acoustical stack of claim 6, wherein the first, second and third thickness are each approximately one-third of the acoustic resonance thickness.

10. The acoustical stack of claim 6, wherein the first and second materials comprise at least one of a composite material and a metal alloy.

11. The acoustical stack of claim 6, wherein the first and second materials are the same with respect to each other.

12. The acoustical stack of claim 6, wherein the first and second materials are different with respect to each other.

13. The acoustical stack of claim 6, further comprising at least a first matching layer configured to be attached to the top side of the first impedance matching layer.

14. The acoustical stack of claim 6, further comprising at least a backing layer configured to be attached to the bottom side of the second impedance matching layer.

15. A method for forming an acoustical stack for a transducer element, comprising:
   defining at least one of a center frequency and a range of operating frequencies associated with an ultrasound transducer;
   identifying an acoustic resonance thickness based on at least one of the center frequency and the range of operating frequencies;
   forming a poled piezoelectric layer of a poled piezoelectric material having a first acoustic impedance and a first thickness, the poled piezoelectric material layer having a top and a bottom; and
   forming at least one impedance matching layer along and joined to one of the top or bottom of the poled piezoelectric material layer, the at least one impedance matching layer formed of a material having substantially the first acoustic impedance and having a second thickness, the first and second thicknesses being combined to form the acoustic resonance thickness.

16. The method of claim 15, wherein the first thickness has an associated output electrical impedance, the method further comprising reducing the first thickness to reduce the output electrical impedance.

17. The method of claim 15, further comprising forming a second impedance matching layer of the material, the second impedance matching layer having a third thickness, wherein the first, second and third thicknesses are combined to form the acoustic resonance thickness.

18. The method of claim 15, further comprising:
   forming a second impedance matching layer of the material, the second impedance matching layer having a third thickness, wherein the first, second and third thicknesses are combined to form the acoustic resonance thickness; and
   adjusting the second and third thicknesses to accomplish wave matching of mechanical and reflected waves.

19. The method of claim 15, wherein the material forming the at least one impedance matching layer comprises piezoelectric material that has the same acoustic impedance as the poled piezoelectric material, the piezoelectric material being unpoled.

20. The method of claim 15, wherein the at least one impedance matching layer is formed of at least one of a composite material or a metal alloy material.

21. The acoustical stack of claim 1, wherein the poled piezoelectric material layer and the first and second impedance matching layers are formed from a same material.

22. The acoustical stack of claim 1, wherein the poled piezoelectric material layer and the first and second impedance matching layers have an equal acoustic impedance value.

* * * * *